United States Patent [19]

Gerber et al.

[11] Patent Number: 4,503,143

[45] Date of Patent: Mar. 5, 1985

[54] ENZYME IMMUNOASSAY WITH TWO-PART SOLUTION OF TETRAMETHYLBENZIDINE AS CHROMOGEN

[75] Inventors: Bego Gerber, Belmont; Elliott Block, Wellesley Hills; Izak Bahar, Worcester; Walter D. Cantarow, Norwood; Mary Coseo, Arlington; Cheryl Eaton, Southboro; Wendy Jones, Sterling Junction; Patricia Kovac, Brookline; John Bruins, Belmont, all of Mass.

[73] Assignee: BTC Diagnostics Limited Partnership, Cambridge, Mass.

[21] Appl. No.: 410,157

[22] Filed: Aug. 20, 1982

[51] Int. Cl.$^3$ .................... G01N 33/54; G01N 33/58; G01N 33/74; G01N 33/76
[52] U.S. Cl. ............................ 435/7; 435/25; 435/28; 435/29; 435/39; 435/810; 436/510; 436/531; 436/817; 436/818
[58] Field of Search .................. 435/7, 25, 28, 29, 39, 435/810; 436/510, 531, 817, 818

[56] References Cited

U.S. PATENT DOCUMENTS 3,791,932 2/1974 Schuurs .................................. 435/7
4,361,648 11/1982 Shuenn-tzong .................. 435/28 X
4,385,114 5/1983 Guthlein .............................. 435/28

FOREIGN PATENT DOCUMENTS 8001972 11/1981 Netherlands .
1464359 2/1977 United Kingdom .

OTHER PUBLICATIONS

Chemical Abstracts, 97: 33481p, (1982).
"Methods in Enzymology", Part A, H. V. Vunakis et al., eds., Chapter 28, by E. Engvall, only pp. 430–432, Academic Press, New York, 1980.

Primary Examiner—Sidney Marantz
Attorney, Agent, or Firm—Barry D. Josephs; Arthur B. Moore; George E. Kersey

[57] ABSTRACT

Colorimetric detection of bindable substances such as antibodies and antigens using chromogens of improved sensitivity and stability. The chromogens take the form of activated solutions containing tetramethylbenzidine or water soluble derivatives of tetramethylbenzidine. Such chromogens are of particular use in home testing applications for detection of antigens such as human chorionic gonadotropin, human luteinizing hormone, and gonococcus bacteria, as well as the detection of antibodies for these substances.

16 Claims, No Drawings

ENZYME IMMUNOASSAY WITH TWO-PART SOLUTION OF TETRAMETHYLBENZIDINE AS CHROMOGEN

BACKGROUND OF THE INVENTION

1. Field of the Invention

The present invention relates to enzyme immunoassay techniques for the detection of bindable substances, such as antibodies and antigens, and particularly in home diagnostic kits. The invention further relates to the use of chromogenic substances in enzyme immunoassays.

2. Description of the Prior Art

There are a number of immunoassay techniques in contemporary use for laboratory detection and measurement of antigens or antibodies present within a test sample. Most of these techniques, however, are unsuitable for use outside a laboratory setting because of complexity of the detection equipment and other difficulties inherent in conducting many conventional immunoassay techniques. Thus, there is a need for a technique suited for home diagnostic immunoassay kits which may be readily used, for example, for the detection of antigens such as human choriogonadotropin hormone (HCG, immunogen) which is present in the urine of pregnant women. In order for a diagnostic immunoassay kit to be satisfactory for home use, the kit must be relatively inexpensive, the immunoassay method must be easy to use, reliable, and efficient, and above all must be safe. Additionally, the test method must be of sufficient sensitivity to easily detect the desired antigen in the test sample.

The earliest conventional immunoassay methods for detection and measurement of antigens or antibodies in a test sample are the radioimmunoassay method (RIA) and the fluorescent immunoassay technique (FIA). In the radioimmunoassay method, the antigen or antibody to be detected is either directly or indirectly labelled with radioactive isotope, commonly an isotope of iodine. Although a radioimmunoassay generally exhibits a high degree of sensitivity even for detection of trace amounts of test antigen or antibody, these tests all involve the use of hazardous radioactive materials which require special handling, storage, and disposal. Also, expensive analytical equipment is required, particularly in radioimmunoassay methods which involve the precipitation of immune complexes, which requires detailed analytical recovery techniques. Solid phase radioimmunoassays circumvent the need for detailed analytical recovery required in the precipitation method, but require much longer incubation times, typically between 30 to 60 hours. Therefore, in view of the potential hazard involved in handling radioactive material, and the need for expensive detection equipment and long incubation times, the radioimmunoassay method is unsuitable for application to home diagnostic kits.

In the immunofluorescence assay the test antigen or antibody may be labelled directly or indirectly by use of fluorescent dyes (fluorochromes) such as fluorescein and rhodamine which can be coupled to the test antigen or antibodies or their immunocomplexes without destroying their specificity. Such conjugates labelled with fluorescent dye can be visualized in a fluorescence microscope. Major disadvantages of the immunofluorescence method either by the direct or indirect method are firstly the dependence on expensive fluorescence microscopes for detecting the labelled conjugate, and secondly, the acknowledged difficulty in quantifying the test antibody or antigen present in the sample. Therefore, the immunofluorescence assay method is unsuitable for use in connection with home diagnostic kits.

In recent years, the enzyme immunoassay method has received increasing attention from researchers for use in detecting and measuring antibodies or antigen in test samples. The enzyme immunoassay methods involve enzyme labelling of the test antigen or antibody either directly or indirectly by labelling immunocomplexes which bind specifically to the test antigen or antibody and which catalyze reaction with a substrate. Some means is provided for monitoring enzyme activity. For example, in the measurement of the enzyme activity of oxidoreductases, one might monitor the oxidation of a chromogenic substance by a substrate such as hydrogen peroxide. Such so-called colorometric assays are readily adapted to the home-testing environment. When the chromogenic substance oxidizes, it forms a chromophore which exhibits visually discernable color changes.

Typical enzyme immunoassays include competitive EIA for antigens, and an enzyme linked immunosorbent assay (ELISA) which also includes direct and indirect ELISA methods. In the competitive EIA method, antigen labelled with enzyme competes with unlabelled sample antigen for binding to a limited quantity of antibodies which have been adsorbed onto a support medium. Once the amount of bound enzyme labelled antigen has been determined, the amount of sample antigen can be determined by the difference between the total amount of antibody bound to antigen less the amount of antibody bound to labelled antigen.

In enzyme immunoassay methods, antibodies specific to the test antigen may be first adsorbed in excess amount onto a solid surface such as a plastic well or tube. The test solution containing antigen is then added; the antigen will bind to the adsorbed antibody. The solid phase, that is the phase composed of all material bound to the antibody, is then thoroughly washed to separate unbound components. Further steps are directed toward quantifying the bound antigen. In the double sandwich antibody ELISA method, an enzyme labelled second antibody, preferably having binding sites different from those of the first antibody, is added and reacts with specific determinant sites on the bound antigen. The enzyme labelled second antibody is added in excess to assure that all the antigen present in the solid phase that is bound to the first antibody will also be bound to enzyme labelled second antibody. The enzyme labelled second antibody molecules will bind in a fixed ratio to each antigen molecule depending on the valence, i.e. specific available binding sites, of the antigen for the second antibody. The solid phase is again washed to remove excess second antibody and any other unbound constituents. An enzyme substrate is then added in solution in excess amount, whereby it makes contact with the bound solid phase. For the enzyme horseradish peroxidase, the substrate may typically be composed of a solution of hydrogen peroxide and a chromogenic material.

o-Phenylenediamine (OPD) heretofore has been acknowledged as one of the most sensitive chromogenic substrates available for detection of peroxidase activity. However, OPD produces a yellowish/orange chromophore which although discernible to the unaided eye is nonetheless not a preferred color for a chromophore, since the eye is more sensitive to other colors in the light spectrum such as blue. Other conventional chromogenic compounds having good sensitivity for peroxidase enzyme detection in enzyme linked immunoassays are o-tolidine and ABTS [2,2'-azinodi(3-ethylbenzothiazolinesulfone-6) diammonium salt]. Although o-tolidine and ABTS have been used successfully for detection of a number of specific antigens using ELISA methods, these latter two chromogenic compounds each have less sensitivity than OPD. All of these chromogenic compounds have been reported as soluble and initially colorless, yielding color change upon oxidation with hydrogen peroxide. Typical enzymes that have been used in the enzyme immunoassay methods are horseradish peroxidase, glucose oxidase, β-D-galactosidase, and alkaline phosphatase. However, since the latter two are found in normal human urine, they are not preferred for use in connection with enzyme immunoassay techniques if they are to be applied in home diagnostic kits. The amount of test antigen present in the solid phase of the double sandwich ELISA method is then directly measurable after the chromogenic substrate has been added, since when there is excess substrate the rate of color change of the chromogen is independent of the substrate concentration and is a function of the total enzyme concentration. The enzyme concentration is a function of the amount of enzyme labelled second antibody, which in turn is a function of the amount of test antigen. Therefore, the rate of color change is a function of the amount of test antigen. The rate of color change can be measured by means of a spectrophotometer if quantification of the amount of test antigen is desired. For use in home diagnostic kits when quantification is not required, the assay should be capable of permitting the user to detect a color change visually which in turn would indicate the presence of a specific antigen in the test sample.

Although the above-described enzyme immunoassay method has been conventionally used in recent years in assaying for antigen or antibodies in a laboratory setting, there has been some difficulty in applying these methods to home diagnostic kits, e.g. for the detection of gonococcus (GC), human chorionic gonadotropin (HCG), or human luteinizing hormone (HLH). Conventional chromogenic reagents preferably are prepared in fresh batches just prior to use, and tend to oxidize and become colored spontaneously when left in storage, typically even for as little as one hour.

In general, a chromogenic compound for detection of enzymes such as horseradish peroxidase should be relatively inexpensive, easy to use in connection with home diagnostic assays, and above all, noncarcinogenic and safe. The chromogenic compound importantly should be stable, soluble, and exhibit rapid color change upon reaction. Also, with substrate, e.g., hydrogen peroxide when exposed to oxidative enzymes, the product chromophore should likewise be safe, stable, and exhibit a high molar absorptivity.

Other chromogenic compounds have been used in pathological studies or assays outside the realm of enzyme immunoassay methods. For example, benzidine has been used to determine peroxidase activity of heme proteins. In such an application, benzidine-hydrogen peroxide chromogenic substrates have been used in forensic medicine for the detection of blood using the peroxidase activity of hemoglobin. Also, benzidine staining procedures have been used to detect the peroxidase activity of the heme proteins cytochrome P-450 and cytochrome P-420. Specifically, the peroxidase activity of these cytochromes has been detected on sodium dodecyl sulfate (SDS)-polyacrylamide-gel electrophoresis by a benzidine staining procedure. Problems have been encountered, however, with the use of benzidine, one of the more important being that it has been found to be a potent human bladder carcinogen. Additionally, staining with benzidine may lack sensitivity. The stain exhibits limited stability, therefore making it difficult to photograph. Researchers in the field of forensic medicine have, therefore, sought alternatives to benzidine for the detection of peroxidase activity of heme proteins, in particular for detection of peroxidase activity of hemoglobin. One such alternative reported in the literature is the use of 3,3',5,5'-tetramethylbenzidine in hydrogen peroxide as a stain for the peroxidase activity of heme proteins, particulary cytochrome P-450. The results of the improved staining procedures using tetramethylbenzidine are reported in P. Thomas, B. Ryan, and W. Levin, *Analytical Biochemistry* 75, 168–176 (1976).

The advantages of using tetramethylbenzidine for the heme staining of cytochrome P-450 as reported in this reference were that the TMB substrates exhibited increased sensitivity, clear dull background, thereby improving color contrast, and greater staining stability, i.e., the TMB stained gels could be stored in the dark at room temperature for at least one month with only minimal loss in TMB stain intensity. In Thomas et al. supra., the improvement in stability of the TMB-hydrogen peroxide staining was reported to be in marked contrast to that obtained with benzidine-hydrogen peroxide where much of the stain is lost within one hour after heme staining for detection of cytochrome P-450. The TMB stained gels were reported to give distinct color even after 25 hours, in contrast to the results obtained with benzidine heme staining wherein much of the color was lost in only one hour after staining.

In the reference Thomas et al. supra., the preferred preparation of the TMB chromogenic solution for detecting the peroxidase activity of cytochrome P-450 on sodium dodecyl sulfate (SDS)-polyacrylamide gel was described as follows: A 6.3mM TMB solution was freshly prepared in methanol. Immediately before use, 3 parts of the TMB solution were mixed with 7 parts of 0.25 M sodium acetate buffer (pH 5.0). After 1 or 2 hours with occasional mixing (every 10–15 min.), $H_2O_2$ was added to a final concentration of 30mM. The staining was visible within 3 minutes when using this solution. After the gels were stained, they were placed in an acetate buffered 30 percent isopropanol solution (i.e. the gels were placed in isopropanol: 0.25 M sodium acetate, pH 5.0 at a ratio of 3:7). This served to clear the gel background and enhance staining intensity and permitted storage of the stained gels in the dark at room temperature for at least 2 months with minimal loss in stain intensity.

The use of alternative solvents for TMB such as ethanol or isopropanol instead of methanol reportedly resulted in diminished stain intensity. The 3:7 ratio of methanol to sodium acetate buffer of pH 5.0 was found to be optimal. When the pH 5.0 sodium acetate buffer was replaced with buffers at pH 4.0, 4.5, 5.5 or 6.0, the stability and sensitivity of staining were significantly reduced.

A salt of tetramethylbenzidine, believed to be noncarcinogenic, namely tetramethylbenzidine dihydrochloride (TMB-d) has been reported in the literature and used as a suitable substitute for benzidine for staining of hemoglobin containing cells and for quantitative determination of hemoglobin in solutions. See, H. H. Liem, et al. *Analytical Biochemistry*, 98, 388–393 (1979). Unlike tetramethylbenzidine, TMB-d is water soluble obviating use of an organic solvent. It also dissolves in 10 percent acetic acid forming a green oxidation product. It has the disadvantage, however, of being unstable in the presence of moisture and air, thereby diminishing its effectiveness.

The use of tetramethylbenzidine-hydrogen peroxide chromogenic substrates as stains for detection of peroxidase activity of heme proteins, such as cytochromes, as reported in Thomas et al., or hemoglobin as reported in Liem is directed to the forensic sciences for detection of blood particularly in samples produced during criminal or accident investigations. The uses of tetramethylbenzidine disclosed in these references, including heme staining and staining of cytochrome or hemoglobulin for application to the forensic sciences, do not extend to the use as a chromogen in enzyme immunoassays.

The use of avidin-biotin complexes (ABC) linked to enzymes such as horseradish peroxidase are disclosed in the literature as increasing the sensitivity of enzyme immunoassays. This technique employs a primary antibody to which is bound test antigen. A biotinylated second antibody then reacts with the bound antigen. An avidin-biotin peroxidase complex (ABC) is prepared and reacts with the biotinylated secondary antibody. The peroxidase will catalyze reaction between chromogen and a substrate such as hydrogen peroxide to produce a color change revealing the presence of the test antigen. This application of the avidin-biotin complex has been used to assay for polypeptide hormones as reported by S. M. Hsu, L. Raine, and H. Fanger, "A Comparative Study of the Peroxidase-Antiperoxidase Method and An Avidin-Biotin Complex Method for Studying Polypeptide Hormones with Radioimmunoassay Antibodies", *Am. J. Clinical Pathology* 7: 734–738 (1981) and in S. M. Hsu and H. J. Ree, "SelfSandwich Method—An Improved Immunoperoxidase Technic for the Detection of Small Amounts of Antigen", *Am. J. Clinical Pathology* 74: 32–40 (1980). Thus, the ABC technique described in Hsu et al. results in a double antibody sandwich with antigen linked between the antibodies and wherein the second antibody is biotinylated; the second antibody in turn is linked to the avidin-biotin peroxidase.

Since the avidin molecule has four binding sites, there are potentially a greater number of enzyme molecules in the complex for each antigen molecule than if enzyme is linked directly to the second antibody. There may be, therefore, a greater sensitivity of this complex to chromogenic substrates since the greater number of enzyme molecules results in increased rate of color change, i.e., increased rate of reaction of chromogen to form color detectable chromophore.

Accordingly, it is an object of the present invention to provide a very sensitive, reliable immunoassay method suitable for use in a home diagnostic kit for detection of antigens.

Another object of the present invention is to provide an improved chromogenic substrate for use in immunoassay techniques for application to home diagnostic kits. A related object of the invention is to provide a safe chromogenic substrate which exhibits increased sensitivity to peroxidase activity, and does not lose its activity prior to use.

SUMMARY OF THE INVENTION

In accomplishing the foregoing and related objects, the invention provides a method for detection of antigen or antibody using colorimetric enzyme immunoassays, particularly assays of the ELISA type. The colorimetric assays of the invention utilize a chromogenic substrate containing tetramethylbenzidine or water soluble chemical derivatives of tetramethylbenzidine. The preferred tetramethylbenzidine is 3,3',5,5'-tetramethylbenzidine and preferred derivatives are water soluble inorganic acid salts of 3,3',5,5'-tetramethylbenzidine, particularly sulphated 3,3',5,5'-tetramethylbenzidine which is the reaction product of concentrated sulfuric acid and tetramethylbenzidine. Another suitable water soluble salt, but somewhat less preferred, is 3,3',5,5'-tetramethylbenzidine dihydrochloride.

It has been determined that tetramethylbenzidine and water soluble derivatives thereof, particularly sulfated 3,3',5,5'-tetramethylbenzidine, exhibit exceptional chromogenic sensitivity and stability making these compounds especially suitable for use in home diagnostic enzyme linked immunoassay methods. TMB possesses superior characteristics as compared with conventional enzyme immunoassay chromogens, providing enhanced sensitivity, with reduced background.

The chromogenic substrates of the invention are suitable for use in a multiplicity of enzyme linked immunoassay methods including competitive, direct, indirect, and inhibition assays. In the preferred embodiment of the invention, the chromogenic substance of the invention is adapted to home diagnostic methods incorporating enzyme linked immunoassays for positive detection of antigens such as human chorionic gonadoptropin hormone (HCG), present in the urine of pregnant women; luteinizing hormone (HLH), elevated in female urine prior to ovulation; and gonococcus bacteria (GC).

The chromogenic substrates of the invention have been successfully tested in a variety of enzyme immunoassays. They have been found particularly successful in a double antibody sandwich enzyme linked immunoassay method, which is well suited to home diagnostic tests for positive detection of antigens such as HCG, HLH hormones, and GC microorganisms. The double antibody sandwich enzyme linked immunoassay method incorporating the chromogenic substance of the invention has the additional advantage that it may be used in clinical or laboratory application for quantitative measurement of such antigens.

The invention also encompasses the use of activated solutions containing organic or inorganic acid salts of tetramethylbenzidine (TMB solution), particularly an activated solution containing sulfated tetramethylbenzidine (TMB-S). The activated solutions contain the TMB component, solvent, buffer, and hydrogen peroxide. A preferred buffer which enhances the stability of the activated solutions is composed of citrate phosphate dissolved in water, having a pH of about 5.0. When the activated solution contains tetramethylbenzidine, the preferred solvent is methanol; however, an activated solution containing instead a water soluble salt of tetramethylbenzidine, such as sulfated tetramethylbenzidine, has an advantage in that it avoids the need for solvents other than water.

The method of the invention when applied in at-home use employs a solid support surface on which the enzyme linked immunoassay is performed. Preliminary assay stages, such as antibody coating of the solid support and blocking of the support surface to prevent nonspecific binding, may be performed in advance of the at-home assay. The improved enzyme immunoassays of the invention combine high sensitivity and reliability, without requiring an involved or time-consuming procedure.

DETAILED DESCRIPTION

The methods herein disclosed use tetramethylbenzidine or its chemical derivatives as chromogenic substances for detection of antigen or antibody in colorimetric enzyme immunoassays. The various immunoassays of the preferred embodiment are of the ELISA type or "enzyme linked immunosorbent assay", which is characterized by the separation of the assay material into solution phase and solid phase components. Various enzyme linked immunosorbent assay methods which may be conducted using the techniques of the present invention are illustrated in A. Voller, et al., "The Enzyme Linked Immunosorbent Assay", Dynatech Laboratories, Inc., Alexandria, Va. (1979) pp. 1-125. These include competitive, direct and indirect, and inhibition immunoassay techniques. The preferred enzyme immunoassay is an ELISA immunoassay using a double antibody sandwich, discussed generally by Voller at pages 13-15.

An important aspect of the invention is the manner of indexing enzyme concentration, which involves a colorimetric technique. In order to detect the subject antibody or antigen, the enzyme immunoassay employs the immunochemical reaction of the assayed substance with one or more antibodies or antigens labelled with enzymes. The assay method permits the concentration of antigen or antibody to be determined from enzyme concentration. The enzyme concentration is determined by monitoring the rate of reaction of the chromogenic substrate producing chromophores. The reaction rate in turn is measurable by monitoring the rate of color change caused by the chromophores. The assay of the invention is preferably performed in a manner that permits proportional indexing between rate of color change and enzyme concentration. Chromogenic substrates which contain 3,3',5,5'-tetramethylbenzidine and its derivatives will provide the required chromogenic sensitivity and reliability. Of special utility are the water soluble derivatives of TMB, particularly, water soluble organic and inorganic acid salts. Preferred water soluble derivatives of tetramethylbenzidine suitable for enzyme immunoassays include 3,3',5,5' tetramethylbenzidine dihydrochloride (TMB-d) and sulfated tetramethylbenzidine (TMB-S). Sulfated tetramethylbenzidine is somewhat more stable than solid tetramethylbenzidine dihydrochloride which has some tendency to oxidize under ambient conditions. Thus, a solution of sulfated tetramethylbenzidine is an especially suitable chromogen for enzyme immunoassays, particularly as applied to home diagnostic methods. All of these compounds have the further advantage of being noncarcinogenic. Chromogens in this family yield distinctive blue chromophores in the presence of hydrogen peroxide and an enzyme such as horseradish peroxidase. Horseradish peroxidase catalyzes the decomposition of the enzyme substrate hydrogen peroxide, the product of which causes the partial oxidation of tetramethylbenzidine to produce blue chromophores. This reaction is characterized by a high extinction coefficient, i.e. dense color per TMB molecule degraded.

Applicants have determined that tetramethylbenzidine and its derivatives, particularly sulfated tetramethylbenzidine, are used most advantageously as enzyme chromogenic substrates for home detection or clinical measurement of antigens when employed in the direct, double antibody sandwich ELISA method. In such applications the user may register the presence of a specific antibody or antigen qualitatively simply by observing the presence of blue color in an immunoassay sample containing even trace amounts of the subject antibody or antigen. This subjective observation may be assessed quantitatively as "positive" when the absorbance or optical density at the maximum absorbance wavelength (in the range 620-700 nm for TMB) exceeds a predetermined threshold level nominally on the order of two standard deviations above a negative threshold, illustratively about 0.04. Thus, the method of the invention may be employed in clinical analysis to obtain quantitative measurement of a specific antibody or antigen in the test sample. Quantitative measurement is obtained spectrophotometrically by reading the absorbance at maximum absorbance wavelength.

Tetramethylbenzidine and its water soluble chemical derivatives, particularly water soluble inorganic or organic acid salts thereof have important advantages over other sensitive chromogens in application to colorimetric enzyme immunoassays. An activated chromogen solution of o-phenylenediamine (OPD) dissolved in hydrogen peroxide shows the characteristic that the OPD chromogen slowly oxidizes to a yellow/orange color when left to stand alone without the presence of enzyme. This must be taken into account when actually conducting the assay in the presence of enzyme. By contrast, solutions of tetramethylbenzidine in hydrogen peroxide or inorganic or organic water soluble salts of tetramethylbenzidine in hydrogen peroxide oxidize to color far less rapidly than the OPD hydrogen peroxide solution. Therefore, there is significantly less background color development in the case of TMB in hydrogen peroxide. Furthermore, solutions of tetramethylbenzidine or its water soluble salts have the additional advantage over OPD solutions in that the TMB solutions are very stable when left alone prior to admixture of hydrogen peroxide, whereas OPD has the tendency to oxidize slowly even when in water solution. Tetramethylbenzidine or water soluble salts thereof have been determined to be significantly more sensitive chromogens than OPD for use in colorimetric enzyme immunoassays. The chromogenic sensitivity of tetramethylbenzidine or its water soluble salts in hydrogen peroxide, as measured by change in absorbance at wavelength of maximum absorbance, is at least three times greater than for OPD chromogen in hydrogen peroxide wherein each chromogen is exposed to the same enzyme concentration and each chromogen is in the optimal concentration of hydrogen peroxide.

Although the present method is applicable to detection or measurement of essentially any type of specific antibody or antigen, the method has been found of particular utility in home diagnostic kits for detection of antigens such as human chorionic gonadotropin hormone (HCG), present in the urine of pregnant women; gonococcus (GC), the bacteria causing gonorrhea; and human luteinizing hormone (HLH), present in female urine at the time of ovulation. The method of the invention has been extended to include clinical detection of the above antigens.

Illustrative TMB solutions for enzyme immunosorptive assays are produced as set forth in Examples 1 and 2 below. The following general conditions apply to the formulation of a suitable chromogen solution. The activated TMB solution should have the maximum amount of TMB chromogen which may be dissolved therein without causing turbidity. If excess chromogen is present the resulting turbidity makes it difficult to read the color intensity of the chromophores spectrophotometrically because of a light scattering effect. Excess organic solvent should be avoided, since such excess could inhibit enzyme activity. In addition, the organic solvent should be within a range to provide satisfactory production of the desired chromophore. Methanol is a preferred organic solvent for such assays.

The principal function of the buffer is to delimit the pH of the activated solution to a range of maximum enzyme activity. Advantageously, the pH range should be between about 4 and 8; more preferably, between about 5 and 6. A suitable buffer pH will depend on the choice of enzyme and the presence of any modifier molecule, as discussed below. The composition of the buffer solution has not been found critical to the present invention, subject to the above constraints.

All water-soluble chromogenic compounds with TMB, such as water soluble acid salts of TMB, are preferred since the use of organic solvents has disadvantages. Most organic water-miscible solvents evaporate easily, thus exposing the user to potential health hazards since many of these solvents are toxic. Solvent evaporation can furthermore cause solution turbidity and deleteriously affect color development. The substrate content (including hydrogen peroxide, in the preferred embodiment) in the chromogen solution should preferably be sufficiently high to saturate the enzyme upon reaction, although hydrogen peroxide may be included in lesser amounts. It is preferred that a saturation quantity of hydrogen peroxide be included in order that the initial rate of color development be directly proportional to enzyme concentration. However, excess hydrogen peroxide should be avoided since it will inhibit enzyme activity. In quantitative measurements of color development, it is advisable to utilize the initial reaction period, during which enzyme activity is most linearly related to enzyme concentration. Measurement may also be made by an end point appraisal after a prescribed reaction period. Although hydrogen peroxide is the preferred enzyme substrate for use with peroxidase, it should be appreciated that other organic peroxides, such as hydroperoxides, may be used which exhibit sufficient specificity for the enzyme particularly methyl hydroperoxide, ethyl hydroperoxide, urea peroxide, or mixtures thereof.

In application of the assay method of the invention for home diagnostic use it is advantageous that the hydrogen peroxide be premixed with the buffer in a first solution and the TMB component premixed with the solvent in a second solution. The user then need only mix these solutions to form the activated TMB solution.

A principal limiting factor of the sensitivity of enzyme immunoassays disclosed herein is the quality of the antisera employed. It is desirable to utilize antibodies of high specificity for the antigen being assayed. In this regard, the use of multispecific systems may decrease assay sensitivity. A preferred source of monospecific antibodies for such assays is found in the hybridoma technique.

In the preferred embodiment of solid phase immunoassay the various assay components are separated between free, solution phase components, and insoluble components bound to solid carriers such as polypropylene tubes, nylon beads, polystyrene microtiter plates, etc. The immunochemically-active components may be covalently bonded to the solid support, cross linked, or physically coupled thereto. For example, in the double-antibody-sandwich assay illustrated in Examples 5 and 8-11, a first antibody is adsorbed to the solid support; the test solution containing suspected antigen is incubated with the sensitized solid support to effect binding of the antigen to the first antibody; an enzyme labelled second antibody specific to the antigen is then incubated with the solid support to effect binding of the enzyme labelled second antibody to the antigen; and finally the substrate added to test for color change of the solid phase. Incubation of the test antigen may be performed simultaneously with incubation of the enzyme labelled second antibody as set forth in Examples 6 and 7. In these and related methods, the amount of bound components are measured to quantify the assay. At each of the various stages, after incubation the supernatant is discarded and the solid phase is washed preparatory to the subsequent step.

In coating the solid support, a procedure is adopted in accordance with the coating characteristic of the immunochemically active material. Most substances will effectively coat by application in solution and incubation for a reasonably brief period. Certain materials, however, such as bacterial suspensions, will not passively adsorb to the solid support, and require a more time-consuming coating procedure whereby the material is allowed to dry on the support surface. In order to reduce nonspecific background staining of the solid support, it may be advisable to apply a blocking agent to the support surface after the initial coating step. In addition the application of the test sample in solution with a buffer and wetting agent, such as PBS/Tween, severely reduces nonspecific binding to the solid phase. In the preferred embodiment of enzyme immunoassay for home diagnostic applications, the initial coating and blocking stages may be performed in advance of the diagnostic test, and the sensitized solid support may be stored with a desiccant material for a period prior to use, in an air-tight, moisture-free environment. The assay kits of such construction exhibit prolonged shelf life of several months with minimal loss of sensitivity.

To establish preferred conditions for coating the solid support, including concentration of reactant, with strength, incubation time, temperature, and pH, preliminary control assays should be conducted with reference reagents, for example with respect to the first antibody in the double antibody-sandwich technique. Control assays are conducted at various antibody concentrations, measuring the color development at each concentration. See Example 3.

Another procedure for quantifying the assays of the invention is conducted to determine the sensitivity to enzyme activity of the given TMB-active solution. These controls should be performed both with the enzyme, and the enzyme-antibody (or antigen) conjugate. Both tests are necessary in that the modified enzyme will characteristically yield an altered enzyme activity. The reaction product (chromophore) is quantitatively measured, using for example a spectrophotometer to measure the absorbance. The specific activity of the various controls is measured by the enzyme dilution required to achieve a given color intensity (see Example 4) or by measuring the initial rate of color development.

The choice of a suitable enzyme preparation for the immunoabsorbent assays of the invention should take a number of factors into account. The enzyme should be of high purity, and its activity should not be inhibited by the assay technique, immunochemical conjugate and test conditions employed. The enzyme should bind firmly to the molecules to be assayed, or to an intermediary such as biotin.

The enzyme should be a stable material, which exhibits a high specificity and turnover rate for the enzyme chromogenic substrate. Additionally, the sample medium (i.e., blood, serum, urine, etc.) should not normally contain the enzyme or its inhibitors. The enzyme should be linked to the antibody or antigen in such a way that each substantially retains its reactivity.

In a single enzyme assay wherein the enzyme used to tag an antibody or antigen catalyzes the chromogenic reaction, suitable enzymes include those classified as oxidoreductase according to the International Union of Biochemists. The more suitable enzymes from this class are those which act on donor groups including —CHOH or —CHNH$_2$ and hydrogen peroxide acceptor. Horseradish peroxidase is a particularly suitable enzyme for diagnostic assays due to the normal absence of enzyme inhibitors in serum and urine.

The enzyme immunoassay techniques of the invention also encompass multiple enzyme systems, which include one or more preliminary stages initially catalyzed by the tagging enzyme. In such multiple enzyme assays, the final chromogenic reaction is catalyzed by an oxidoreductase enzyme. Such multiple enzyme systems may be used, for example, to provide a cascade effect wherein successive stages provide increased turnover of the substrate.

In order to maintain a high signal-to-noise ratio in the colorimetric readings, one should minimize the occurrence of spurious reactions with substances which might commonly be encountered in the test serum, urine, etc. It is desirable for this reason to perform test assays with control samples to determine the background effect of such reactions.

A particular problem in the detection of labelled enzymes in immunoassays is the fact that the binding of the enzyme protein to the assayed molecule will modify the activity of both constituents. This can lead to a severe decrease in assay sensitivity. It may be advantageous to include a coupling reagent between the enzyme and antibody to increase assay sensitivity by reducing steric interference of the conjugate molecules. In a preferred embodiment of the invention, as illustrated in Example 9, a complex is formed of the enzyme horseradish peroxidase with avidin and biotin. This complex provides a plurality of enzyme binding sites, so that when the ABC molecule is coupled to the second antibody in the double-antibody-sandwich, the complex will include a high enzyme concentration, providing a marked increase in chromophore production. This coupling agent provides high optical density signals at reasonably low conjugate concentrations and incubation times, with little or no nonspecific background staining. Other suitable coupling reagents include glutaraldehyde and sodium periodate.

The invention is not intended to be limited to any particular class of antibody used in specific binding to antigen, and requires only that the antibody exhibits the requisite degree of specificity for the antigen. In the double-antibody sandwich-type assays, if the antigen to be assayed is HLH or HCG hormone, the first and second antibodies may be prepared in like manner typically from mouse monoclonal or rabbit polyclonal antisera generated from innoculation of mouse or rabbit with the test antigen HLH or HCG. The polyclonal antibodies are typically purified by three successive ammonium sulphate precipitations or by Ultrogel AcA 34 column chromatography (Ultrogel AcA 34 is a tradename of LKB Instruments, Inc., Rockville, MD). The second antibody normally binds the antigen molecule at binding sites which are of a different type than the binding sites at which the first antibody binds to the antigens. These first and second antibodies are typically used interchangeably in the assay. In the double antibody sandwich ELISA assay of the preferred embodiment, the first antibody need not be specific for the antigen to be detected; generally, an immunoglobulin fraction containing the specific antibody can be used. If the antigen to be assayed is GC microorganism, the first and second antibodies may be prepared in like manner typically from mouse monoclonal or polyclonal antibody generated from innoculation of mouse with the GC antigen. In this case, the first and second antibodies need not be directed against different binding sites on the antigen molecule. These first and second antibodies may also typically be used interchangeably in the assay. It should also be appreciated that other binding materials such as lectin can be used in place of either the first or second antibody or wherever else antibodies are used in the assay whether to coat the support or to link the assay antigen to enzyme so long as this substance provides desired binding specificity.

The enzyme immunoassay techniques of the invention are further illustrated in the following non-limiting examples in which all proportions are by weight unless otherwise specified:

EXAMPLE 1

An activated TMB solution was prepared by mixing 4.0 parts by volume of reagent (i) with 11.0 parts by volume of reagent (ii), and then adding 0.010 part by volume of the 30 percent hydrogen peroxide solution (reagent (iii)). The mixture was stirred to form a homogenous, activated TMB solution. The individual reagents were produced as follows:

Reagent(i)

Reagent(i) was prepared by dissolving 1.25 g (5.20 mMol) of 3,3',5,5'-tetramethylbenzidine in 1.00 liter absolute methanol with or without heating. A clear colorless or faintly tan solution resulted which could be stored for at least six weeks in a brown bottle without affecting its usefulness.

Reagent(ii)

Reagent(ii) is a buffer prepared by first dissolving 144.8 grams (1.020 mol) of disodium hydrogen phosphate in 1.00 liter hot deionized water. The phosphate dissolved in the hot deionized water upon stirring. To this solution 102.95 grams (0.4902 mol) of citric acid monohydrate were added. The resulting solution was then diluted to 10.0 liters with additional deionized water, thus forming a citrate-phosphate solution, with a pH of 5.0.

Reagent(iii)

Reagent(iii) consisted of an aqueous solution of hydrogen peroxide, wherein the $H_2O_2$ comprised 30 percent by volume.

EXAMPLE 2

A method of preparing an activated solution containing sulfated tetramethylbenzidine (TMB-s Solution) for use in enzyme linked immunosorbent assays is given as follows:

Sulfated TMB:

Sulfated tetramethylbenzidine was first prepared by dissolving 0.50 grams of tetramethylbenzidine in 55 ml of diethyl ether at room temperature. Fifty microliters of concentrated sulfuric acid was added to this solution, forming immediately a white precipitate of sulfated TMB. The white precipitate of sulfated TMB was separated from the mixture by conventional filtration or decantation. (A further fifty microliters of concentrated sulfuric acid were added to the filtrate; no additional precipitate formed.) The recovered precipitate was then washed twice with fresh ether by mixing the precipitate in the ether for about 30 minutes per elution. The ether mixture was then allowed to dry in air. As the ether evaporated, 30 mg of light tan crystals of sulfated tetramethylbenzidine were recovered. The chemical formula of the resulting sulfated TMB product is not yet established with certainty but is believed to embrace any or all of the following formulas, and most characteristically the first: $TMB.H_2SO_4$, $TMB.2H_2SO_4$, and $(TMB)_2.H_2SO_4$.

TMB-s Solution:

An activated solution of sulfated tetramethylbenzidine (TMB-s Solution) was prepared in a similar manner to that set forth in Example 1, except that methanol was not used as a solvent since TMB-s is water soluble.

The activated TMB-s solution was prepared by mixing 5.0 mg of sulfated tetramethylbenzidine (TMB-s) into 1.0 ml of deionized water. Essentially all of the TMB-s dissolved in the deionized water upon mixing, leaving a solution of only slight turbidity. To 0.250 ml of this solution were added 3.5 ml of the citrate-phosphate buffer reagent(ii) of Example 1. After mixing for a short period, there was no visible precipitate. To this mixture was added 25 ml of 3 percent hydrogen peroxide aqueous solution.

The resulting mixture was an activated TMB-s solution ready for use as a chromogenic substance for enzyme linked immunosorbent assays. The total concentration of TMB-S and hydrogen peroxide in this TMB-S solution was equivalent to the concentration of TMB and hydrogen peroxide present respectively for the TMB solution prepared in Example 1.

EXAMPLE 3

Preliminarily to conducting various double-antibody sandwich ELISA's e.g. as in Example 5, the following steps were taken to determine the extent of coating of mouse antibody to the support surface as a function of antibody concentration. Solutions of varying concentrations of the given mouse antibody in suitable buffer such as phosphate buffered saline (PBS) were added to different wells of a polystyrene microtiter plate. The phosphate buffered saline (PBS) contains no calcium and is available from GIBCO Laboratories, Grand Island, NY. These solutions were maintained at 23° C. ±2° C. for one hour to effect adsorption of the mouse antibody to the support surface. The microtiter plates were then decanted and filled with a blocking solution of 0.5 gm. of bovine serum albumin (BSA Cohn Fraction V, supplied by Sigma Chemical Co., St. Louis, Mo.); 0.02 gms. of sodium azide ($NaN_3$); dissolved in 100 ml of calcium free phosphate buffered saline (PBS). This solution was allowed to remain in the wells for about 30 minutes at 23° C. The solution was decanted and the plates eluted twice with polyoxyethylenesorbitan monolaurate available under the tradename Tween-20 buffer from Sigma Chemical Company, St. Louis, Mo.

A suitable dilution (one giving negligible nonspecific binding) of an antibody-horseradish peroxidase conjugate such as goat anti-mouse immunoglobulin*-horseradish peroxidase conjugate was then added to the wells and left to incubate for a period of about 15 minutes to effect specific binding of the conjugate to the mouse antibody.

* Goat antisera generated from innoculation of goat with mouse immunoglobulin

After elution as above, a fixed quantity of the TMB-s solution of Example 2 was added. The rate of color development of each sample was measured as a function of the coating antibody concentrations to determine which antibody concentrations gave the best color development.

EXAMPLE 4

The following procedure was effected to assay horseradish peroxidase activity with respect to the activated TMB-s solution of Example 2. Twenty microliters of horseradish peroxidase (type VI, from Sigma Chemical Company) was added to a dry polystyrene cuvette. One milliliter of TMB-s activated solution was added to the test tube, which was then incubated at room temperature for 5–10 minutes. The reaction product was measured using a Uvikon 810 spectrophotometer of Kontron, Inc., Redwood City, Calif., recording the absorbance at 660 nanometers (nm). The initial rate of blue color development at 660 nm was directly proportional to the concentration of enzyme. The time period in which such direct proportionality was observed was up to about one minute. Thereafter, the rate of color change tapered off, and maximum color intensity was observed after about 90 minutes.

The above procedure was repeated for various lots of peroxidase comparing their specific activities. The activities of different TMB-s samples may be quantified similarly.

EXAMPLE 5

The following protocol is not limited to specific types of antigen; however, it has been found particularly suitable as a double sandwich enzyme immunoassay for human luteinizing hormone (HLH) and human chorionic gonadotropin hormone (HCG). The procedure involved coating the support plate with a first antibody, adding the antigen sample, and then a second antibody-enzyme conjugate. The first and second antibodies in the various assays were obtained from monoclonal hybridoma antibodies prepared from innoculated mice or polyclonal antisera generated by the innoculation of rabbits with the test antigen. The antisera were purified by successive precipitations with ammonium sulfate.

Wells of a polystyrene microtiter plate were coated with the first antibody: a coating antibody solution was added to each well, and this was incubated for 1–4 hours at room temperature, then decanted. Three hundred microliters of a PBS/0.5% BSA blocking solution (0.5 gm bovine serum albumin per 100 ml of phosphate buffered saline) were added to the wells and incubated for thirty minutes. The wells were then decanted and twice washed with PBS/Tween buffer. The PBS/Tween buffer was composed of 0.1 vol. percent Tween Solution and 99.9 vol. percent PBS.

A solution to be tested for antigen was added to the wells and incubated. The incubation times were thirty minutes for HCG and one hour for HLH. The wells were then decanted and washed with PBS/Tween buffer.

A solution of horseradish peroxide-conjugated second antibody, which may typically be conjugated with glutaraldehyde or avidin-biotin was added to the wells, and incubated for thirty minutes at room temperature. After decanting and washing with PBS/Tween buffer, 150 microliter of the TMB-s activated solution of Example 2 were added. The chromogen-containing solution was allowed to incubate for between 5 and 30 minutes, then an absorbance reading was taken at 660 nanometers (nm) using a Dynatech Microelisa MR 580 Autoreader, available from Dynatech Laboratories, Alexandria, Va. The protocol set forth in Example 5 was used successfully to detect HCG hormone at concentrations as low as 7.8 nanograms/ml. and HLH at concentrations as low as 7.8 nanograms/ml.

The rate of color development, as measured by change in absorbance of the activated TMB-s solution at wavelength of maximum absorbance, 660 nm, was at least three times greater than that achieved with the use of the chromogen o-phenylenediamine (OPD) dissolved in its optimum hydrogen peroxide concentration. (The absorbance of OPD color change was also measured at its wavelength of maximum absorbance.) The rate of color development using the activated TMB-s solution of Example 2 is faster than that obtained using the activated TMB solution of Example 1.

EXAMPLE 6

The double-antibody sandwich ELISA assay of Example 5 was repeated for HCG with the following modifications. The antigen solution and enzyme-conjugated second antibody were added and incubated simultaneously. The incubation time was thirty minutes for HCG. This abbreviated assay provided results comparable to those of Example 5, and resulted in at least three times faster color development than would occur if OPD chromogen were used in this same assay under optimal hydrogen peroxide concentration. The protocol set forth in Example 6 was used successfully to detect HCG hormone at concentrations as low as 7.8 nanograms/ml. (urine).

EXAMPLE 7

The following protocol was carried out as a double-antibody sandwich ELISA for gonococcus (GC) bacteria wherein the antigen solution and second antibody were added and incubated simultaneously.

The wells of a polystyrene microtiter plate were passively coated in appropriate dilution with mouse anti-GC (monoclonal antibodies generated by hybridoma using GC membranes or whole cells as antigens) in high ionic strength 0.4 M NaCl PBS. The solution was incubated for 1 hour at 37° C. to effect adsorption of the antibody onto the microtiter plate, and the liquid decanted. Remaining adsorption sites were blocked by incubating for 30 minutes with 300 microliters of PBS/0.5% BSA. The blocking agent was decanted, and the wells twice washed with PBS/Tween buffer.

Fifty microliters of a urogenital sample suspected to contain GC antigen were added, along with 5 microliters of mouse anti-GC conjugated to peroxidase (a conjugate of peroxidase and mouse antibody directed against GC antigen). These were mixed using slight agitation, and incubated for two hours at room temperature. The well contents were then decanted, and the well washed thrice using PBS/Tween buffer.

One-hundred and fifty microliters of activated TMB-s solution, from Example 2, were added and incubated for 30 minutes. The absorbance at 660 nm was then recorded using a Dynatech reader.

The entire immunocomplex attached to the coated surface may be represented schematically by the formula:

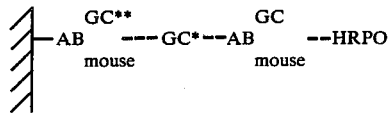

*Antigen being assayed.
**$AB_x{}^y$ = antibody to y raised in animal x.

The protocol set forth in Example 7 was successfully used to detect gonococcal concentration levels as low as 5,000 gonococcal cells per milliliter.

EXAMPLE 8

The double antibody sandwich ELISA for GC of Example 7 was repeated with the following modification, to effect a sequential assay:

Fifty microliters of the test sample were added without enzyme-conjugated antibody. This was incubated for 2 hours at 37° C., decanted, and the wells thrice washed with PBS/Tween buffer.

Fifty microliters of peroxidase-conjugated rabbit anti-GC (peroxidase conjugated to rabbit antibody directed against GC antigen) was then added in an appropriately diluted solution with PBS/BSA/Tween (0.5 gms. BSA per 100 ml PBS and 0.1 ml Tween). This solution was incubated for 30 minutes at room temperature, decanted, and the wells eluted as above.

The nonsimultaneous double sandwich ELISA for GC of Example 8 was used successfully for the detection of gonococcal cells at concentrations of 50,000 cells/ml.

EXAMPLE 9

A double antibody sandwich ELISA assay for HLH antigen, using monoclonal antibodies, was conducted to effect a sequential assay as follows:

Wells of a polyvinyl chloride microtiter plate were coated with 100 microliters of HLH nonspecific monoclonal antibody obtained from mouse hybridoma cell culture, and appropriately diluted with PBS buffer. The antibody solution was incubated for 1 hour at room temperature. Residual binding sites were then blocked with PBS/0.5% BSA/0.02% sodium azide buffer (0.5 gms BSA and 0.02 gm sodium azide per 100 ml PBS), which was incubated for 30 minutes at room temperature followed by repeated elutions with PBS/Tween buffer.

A calibration curve was developed using a titration of HLH in PBS/Tween buffer. Fifty microliters of HLH antigen solution were added to the top half of the plate leaving the bottom half as a negative control. The sample was incubated for 1 hour, followed by three washes with PBS/Tween buffer.

One hundred microliters of biotinylated rabbit anti-HLH polyclonal antibody were added in appropriate concentration, incubated for 30 minutes, and thrice washed with PBS/Tween buffer. To this biotinylated antibody was added a preformed avidin-biotin horseradish peroxidase complex (ABC) from Vector Laboratories, Burlingame, Calif.

One-hundred and fifty microliters of activated TMB solution from Example 1 were added and incubated for 15 minutes, and the absorbance at 660 nm recorded.

This procedure was successfully employed to detect HLH antigen at concentrations at least as low as 8 nanograms/ml.

The entire immunocomplex attached to the coated surface may be represented schematically by the formula:

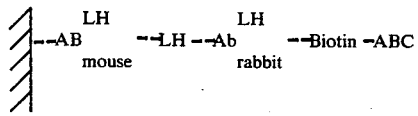

EXAMPLE 10

The following protocol was effected to assay for antibody directed against gonococcus bacteria:

Individual wells of polyvinyl chloride microtiter plates were coated with 50 microliters of GC suspension. These were allowed to dry overnight at 37° C. and/or dried in a dessicator for 1–2 hours and then fixed by adding 300 microliters of methanol to each well for 10 minutes. Each well was then twice washed using PBS/Tween buffer, blocked by incubating 30 minutes at room temperature with 300 ml per well of PBS/0.5% BSA/0.02% sodium azide. The wells were then washed twice with PBS/Tween.

Fifty microliters of mouse anti-GC bacteria were added to each well in appropriate dilution. This was obtained from spent cell culture fluid containing antibody secreted by mouse hybridoma cells or from ascites fluid or from polyclonal rabbit serum. The antibody solution was incubated for 1 hour at room temperature, and thrice washed with PBS/Tween buffer.

One-hundred microliters of peroxidase conjugated goat anti-mouse Ig was added in solution with PBS/BSA/Tween, appropriately diluted. The section was incubated for 30 minutes to 1 hour, then thrice washed with PBS/Tween.

One-hundred and fifty microliters of activated TMB solution, prepared in accordance with Example 1, were added and incubated for 30 minutes, after which an absorbance reading at 660 nm was recorded with a Dynatech reader from Dynatech Laboratories, Alexandria, Va.

The foregoing protocol was used successfully to detect mouse anti-GC at concentrations as low as 800 nanograms/ml.

The entire immunocomplex attached to the coated surface may be represented schematically by the formula:

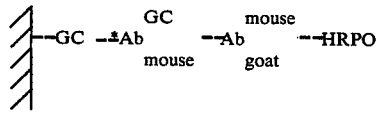

*Antibody being assayed. ($Ab_x^y$ = antibody to y raised in animal x.)

EXAMPLE 11

The ELISA protocol of Example 10 was repeated but instead to assay for antibodies directed against HLH antigen (human luteinizing hormone). The protocol of Example 10 was followed except for the following modifications. The initial coating was effected with a 7.4 pH solution of HLH antigens in PBS. The antigen solution was incubated overnight at 4° C. The sample to be assayed was 50 microliters of appropriately diluted ascites fluid or undiluted cell culture supernatant fluid.

The foregoing protocol was used successfully to detect mouse anti-HLH.

The entire immunocomplex attached to the coated surface may be represented schematically by the formula:

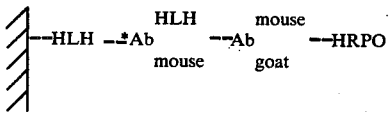

*Antibody being assayed. ($Ab_x^y$ = antibody to y raised in animal x.)

The assay methods set forth in the illustrative examples 5–11 may be applied in a home diagnostic assay kit. For example, a number of vials containing the various immunologic reagents required for the assay may be included in a kit. The user need then only mix these reagents with the test sample in accordance with a given protocol and await a color change in the final solution. One method of application of the double antibody sandwich ELISA to a home diagnostic kit could be effected, illustratively, by providing the kit with one vial (vial 1), which has been precoated with a first antibody and blocking solution and a second vial (vial 2) which would contain a solution of the second antibody—enzyme conjugate. Another vial (vial 3) could contain a solution of the chromogen and solvent, and an additional vial (vial 4) could contain the solution of buffer and hydrogen peroxide. In carrying out the assay, the user need only collect a urine specimen suspected of containing the antigen to which the assay is directed. The user may take a sample of the urine with a dropper supplied in the kit and may add a few droplets to vial 2. The contents of vial 2 would be immediately transferred to vial 1 and the contents therein allowed to incubate for a prescribed period at room temperature. The user could therupon discard the liquid contents in vial 1 and rinse the remaining contents several times with cold tap water. The contents in vial 4 could then be mixed into the contents of vial 3 to form an activated chromogenic solution in vial 3. The user could then easily transfer the activated chromogenic solution from vial 3 to vial 1 whereupon the user could wait another prescribed period of time and then observe whether the contents of vial 1 have developed a blue color, thus confirming the presence of the antigen being assayed.

It should be appreciated that the foregoing procedure is merely illustrative.

Although the preferred application of the chromogenic compound of the invention has been illustrated in the foregoing detailed description in the context of certain specific enzyme linked immunosorbent assays, it should be appreciated that the chromogen is equally applicable to any type of enzyme immunoassay. Although the various specific assays illustrated in the above detailed description are in the human diagnostic category, the enzyme immunoassays of the invention may be extended to veterinary applications, such as the detection of horse chorionic gonadotropin. Accordingly, the invention is not intended to be limited to the specific embodiments or examples set forth in the specification, but rather is defined by the claims and equivalents thereof.

We claim:

1. An enzyme immunoassay for the colorimetric detection of an antigen of the type wherein a quantity of a first antibody is adsorbed to a solid support; a conjugate is formed between an immunologic reagent and an enzyme; said conjugate is admixed with a sample to be tested for an antigen, said antigen binds to said first antibody and to said conjugate to form an immunologic complex in solid phase; and the quantity of said antigen is determined by measuring the reaction of said immunologic complex with a chromogenic substance responsive to said enzyme, wherein the improvement comprises:

providing a first liquid solution comprising a tetramethylbenzidine and an organic solvent and a second liquid solution comprising a peroxide and buffer, mixing said first and second liquid solutions to form an activated liquid solution of a tetramethylbenzidine approximately just prior to determination of antigen in said test sample, said activated liquid solution forming the chromogenic substance.

2. An enzyme immunoassy as in claim 1 wherein the first liquid solution consists essentially of a tetramethylbenzidine and an organic solvent and the second liquid solution consists essentially of a peroxide and a buffer.

3. An enzyme immunoassay as in claim 1 wherein the buffer in said second liquid solution is a citrate-phospate aqueous buffer yielding a pH of the activated liquid solution of between about 4 and 8.

4. An enzyme immunoassay as in claim 1 wherein the antigen is selected from the group consisting of human chorionic gonadotropin, luteinizing hormone and gonococcus bateria.

5. An enzyme immunoassay as in claim 1 wherein the organic solvent for the tetramethylbenzidine is methanol.

6. An enzyme immunoassay as in claim 5 wherein the methanol solvent comprises about one third by volume of the activated liquid solution.

7. An enzyme immunoassay as in claim 1 wherein the enzyme comprises an oxidoreductase.

8. An enzyme immunoassay as in claim 7 wherein the enzyme is a peroxidase.

9. A diagnostic kit for carrying out an enzyme immunoassay of an analyte comprising the following separately contained components:

(a) a solid support precoated with a first antibody;

(b) a solution comprising a conjugate of an enzyme with a second antibody;

(c) a solution comprising a tetramethylbenzidine and a solvent; and (d) a solution comprising a buffer and a peroxide.

10. The diagnostic kit as in claim 9 wherein the solid support of (a) is also precoated with a blocking solution.

11. The diagnostic kit as in claim 9 wherein the peroxide of (d) is hydrogen peroxide.

12. The diagnostic kit as in claim 9 wherein the enzyme of (b) is an oxidoreductase.

13. The diagnostic kit as in claim 9 wherein the enzyme of (b) is a peroxidase.

14. The diagnostic kit as in claim 9 wherein the solvent of (c) is methanol.

15. The diagnostic kit as in claim 9 wherein the buffer of (d) is an aqueous citrate-phosphate buffer.

16. The diagnostic kit as in claim 9 wherein the analyte being determined is selected from the group consisting of human chorionic gonadotropin, luteinizing homone and gonococcus bacteria.

* * * * *